(12) United States Patent
Lell et al.

(10) Patent No.: US 10,695,494 B2
(45) Date of Patent: *Jun. 30, 2020

(54) NEEDLELESS INJECTION DEVICE HAVING A GEL AND A MEMBRANE

(71) Applicant: Peter Lell, Moosburg (DE)

(72) Inventors: Peter Lell, Moosburg (DE); Julia Engert, Munich (DE); Cihad Anamur, Ludwigshafen (DE); Christian Fellner, Ilmmünster (DE); Gerhard Winter, Penzberg (DE)

(73) Assignee: Peter Lell (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/519,858

(22) PCT Filed: Oct. 22, 2015

(86) PCT No.: PCT/EP2015/074534
§ 371 (c)(1),
(2) Date: Apr. 18, 2017

(87) PCT Pub. No.: WO2016/062825
PCT Pub. Date: Apr. 28, 2016

(65) Prior Publication Data
US 2017/0246391 A1    Aug. 31, 2017

(30) Foreign Application Priority Data
Oct. 22, 2014  (EP) .................... 14189971

(51) Int. Cl.
*A61M 5/20* (2006.01)
*A61M 5/30* (2006.01)

(52) U.S. Cl.
CPC ........ *A61M 5/2046* (2013.01); *A61M 5/3015* (2013.01); *A61M 5/30* (2013.01); *A61M 2207/00* (2013.01)

(58) Field of Classification Search
CPC .............. A61M 5/2046; A61M 5/2053; A61M 5/3015; A61M 5/30; A61M 2207/00; C06B 45/12; C06B 23/00
See application file for complete search history.

(56) References Cited

U.S. PATENT DOCUMENTS

| | | |
|---|---|---|
| 3,308,818 A | 3/1967 | Rutkowski |
| 5,399,163 A | 3/1995 | Peterson et al. |

(Continued)

FOREIGN PATENT DOCUMENTS

| | | |
|---|---|---|
| DE | 102007004211 A1 | 7/2008 |
| EP | 1557190 A1 | 7/2005 |

(Continued)

OTHER PUBLICATIONS

Lell, Peter, Translation of WO-2004071558-A1, Aug. 2004 (Year: 2004).*

(Continued)

*Primary Examiner* — Emily L Schmidt
(74) *Attorney, Agent, or Firm* — Faegre Drinker Biddle & Reath LLP

(57) ABSTRACT

The invention relates to a needleless injection device, comprising a firing chamber (11) for the needleless injection of a substance (25), having a firing chamber containing a pyrotechnic material and a gel-like medium, with which a substance, in particular an active substance, can be accelerated at high speed and injected in a needleless manner into a tissue or into a body by means of a membrane (15).

The invention also relates to a method for producing a needleless injection device of this type containing a firing chamber together with pyrotechnic material and filled with a gel-like medium, and use thereof.

10 Claims, 2 Drawing Sheets

(56) References Cited

U.S. PATENT DOCUMENTS

| | | | |
|---|---|---|---|
| 6,258,063 B1 * | 7/2001 | Haar | A61M 5/2425 222/633 |
| 7,160,265 B2 | 1/2007 | Lell | |
| 7,981,075 B2 | 7/2011 | Alexandre et al. | |
| 8,262,604 B2 | 9/2012 | Asmussen et al. | |
| 2002/0188248 A1 * | 12/2002 | Bellhouse | A61M 5/3015 604/68 |
| 2003/0114789 A1 * | 6/2003 | Haar | A61M 5/30 604/69 |
| 2010/0179473 A1 * | 7/2010 | Genosar | A61M 5/14248 604/70 |
| 2011/0230826 A1 * | 9/2011 | Yoh | A61M 5/30 604/70 |
| 2013/0327454 A1 * | 12/2013 | Twomey | C06B 31/30 149/4 |
| 2016/0213882 A1 * | 7/2016 | Fitterer | A61B 17/3207 |

FOREIGN PATENT DOCUMENTS

| | | | |
|---|---|---|---|
| FR | 2875413 A1 | 3/2006 | |
| WO | WO-9831409 A2 | 7/1998 | |
| WO | WO-0003758 A1 | 1/2000 | |
| WO | WO-2004071558 A1 * | 8/2004 | A61M 5/3015 |
| WO | WO-2004074558 A1 | 9/2004 | |

OTHER PUBLICATIONS

International Search Report for PCT/EP2015/074534 dated Feb. 4, 2016.

Written Opinion of the International Searching Authority for PCT/EP2015/074534 dated Feb. 4, 2016.

* cited by examiner

NEEDLELESS INJECTION DEVICE HAVING A GEL AND A MEMBRANE

CROSS-REFERENCE TO RELATED APPLICATIONS

This application is a national stage application (under 35 U.S.C. § 371) of PCT/EP2015/074534, filed Oct. 22, 2015, which claims benefit of European Application No. 14189971.6, filed Oct. 22, 2014, both of which are incorporated herein by reference in their entirety.

The invention relates to a needless injection device, comprising a firing chamber for the needless injection of a substance, having a firing chamber containing a pyrotechnic material and a gel-like medium, with which a substance, in particular an active substance, can be accelerated at high speed and injected in a needleless manner into a tissue or into a body by means of a membrane. The invention also relates to a method for producing a needless injection device of this type containing a firing chamber together with pyrotechnic material and filled with a gel-like medium, and use thereof.

A successful injection lies in the fact that sufficient substance is introduced into the body through the tissue or body barrier, in particular such as the skin of humans or animals. The basic principle of injecting a medium in a needleless manner by means of high pressure has been known for some time (for example see U.S. Pat. No. 3,308,818).

Various types of needleless injection devices are described in the prior art, for example (not exhaustively) a cylinder-piston unit comprising a pretensioned spring element (DE 10 2007 004 211 A1) or by means of what are known as injection cartridges (WO 98/31409) and by means of a gas cartridge for acting on a piston (U.S. Pat. No. 5,399,163).

Furthermore, needleless injection devices can contain a pyrotechnic drive, which for example is used to actuate a piston and in this way causes an active substance to be pressed out from a cannula (EP 1 557 190 A1).

A further embodiment of a needleless injection device operated pyrotechnically lies in the fact that an explosion is generated in a chamber (also referred to as a firing chamber), wherein the released energy acts on a membrane such that a membrane-bound substance adsorbed outwardly in the direction of the target tissue is sufficiently accelerated and detaches from the membrane in the direction of the target tissue.

A device of this type is disclosed for example in WO 2004/071558 A1. However, a generic embodiment of this type can still be improved, such that a desired substance can be introduced into a body in an improved manner.

The present invention therefore makes reference to a generic embodiment according to WO 2004/071558, but addresses the objective problem of improving the needle-free injection.

The present invention therefore relates to a needleless injection device comprising a (firing) chamber (11) having a) at least one pyrotechnical material (24a) and b) at least one gel-like medium (24b), wherein the chamber (11) has a least one membrane (15) at a discharge opening and is provided with a substance application (25).

The firing-chamber-side membrane (13) leads to the firing chamber (11) and combustion chamber (24) thereof.

Within the scope of this invention, a "gel-like medium" or a "gel" is understood to mean a mixture of at least one liquid (Lyogel) with at least one gelling agent, which mixture leads to an increase of the viscosity of the otherwise less-viscous liquid. Preferred liquids are hydrophohic liquids in accordance with the invention. The gel-like medium is more preferably present in a phase. In addition, the gel-like medium (24b) is chemically different from the pyrotechnic material (24a). The gel-like medium (24b) is not identical or equal to the pyrotechnic material (24a) and has a viscosity different from the pyrotechnic material (24a).

In accordance with the invention, various liquids and various gelling agents are possible. However, hydrophobic liquids, such as (not exhaustively) oily liquids such as vegetable or animal oils, triglycerides, mono- and diglycerides, phospholipids, liquid waxes, alcohols, silicone oils, paraffins and other low-volatile hydrophobic substances, are preferred. Solid and semi-solid and liquid gelling agents of inorganic and organic nature are conceivable. The gelling agents can be hydrophilic, amphiphilic, and lipophilic in nature. Such gelling agents in accordance with the invention can be (not exhaustively): pectin, tragacanth, polyacrylic acids, polyvinylpyrrolidone, silicon dioxide, highly dispersed silicon dioxide, carboxymethylcellulose, carbomers (polyacrylic acid), cellulose ethers, poloxamers (gels, viscous solutions). The resultant gel-like media can be present for example and preferably in the form of oleogels, lipogels, silicone oil gels or paraffin gels.

Liquid, inert hydrophobic liquids, such as oils (glycerides) and silicone oils, can be used preferably together with solid gelling agents.

It has surprisingly been found that, with a gelling agent, thickened hydrophobic liquids cannot only be metered into the firing chamber more easily and more reliably, but at the same time the function of the device and reliability thereof can be improved. It has also surprisingly been found that in particular silicone oil gels which are thickened using hydrophilic silicon dioxide enable particularly advantageous combinations of handling during the production and functionality of the device when used as intended. The gel-like medium used in accordance with the invention advantageously causes an optimisation of the shock wave or pressure wave at the membrane and at the same time makes it possible to minimise the required amount of pyrotechnic material (24a).

The use of silicon dioxide, in particular highly dispersed silicon dioxide (for example Aerosil R200 Pharma, Aerosil R972 Pharma (Evonik, Germany)), preferably in conjunction with a viscous liquid, such as silicone oil, is very particularly preferred for the gelling (thickening) of hydrophobic liquids. It is also preferred that an oleogel, in particular a silicone oleogel, is present after the thickening.

Gels which consist of silicone oil and highly dispersed silicon dioxide are therefore also preferred. Gels which are produced from hydrophilic highly dispersed silicon dioxide and silicone oil are particularly preferred.

The resultant gel can be runny, viscous, or solid. A viscosity at which the device according to the invention can be produced in an advantageous manner is preferred. Here, it should be ensured that the correctly metered amount is introduced into the combustion chamber. In one embodiment, the gel is runny and by way of example is metered into the chamber by means of a pouring method. In another embodiment, the gel is viscous and is metered, spread or otherwise introduced into the chamber by means of a method in which it is poured or added in drops. In a further embodiment, the gel is semi-solid to solid, but resilient and is inserted, placed or otherwise introduced into the chamber in one go.

Here, the gel can be introduced in one portion, in a number of small portions, or in a smaller number of larger portions.

It is particularly preferred that the empty volume of the firing chamber is filled to the greatest possible extent with the gel-like medium according to the invention, preferably with a viscous or thick hydrophobic material, so that the shockwave or pressure wave emanating from the pyrotechnic material is coupled in an optimal way to the membrane and at the same time the amount of pyrotechnic material necessary for this can be minimised.

Here, the entire volume of the firing chamber is advantageously taken up by the gel-like medium according to the invention, such that no gas spaces or only few gas spaces remain prior to the ignition of the pyrotechnic material.

Here, it is advantageous that the gel-like medium itself does not contain any gaseous inclusions or impurities—i.e. is gas-free—or only contains a small amount of gaseous inclusions or impurities.

It is also advantageous that methods which prevent or reduce the presence of gaseous inclusions or which provide a gas-free gel-like medium are applied during the production of the gel-like media.

It is additionally advantageous at the time of production of the gel-like media, in particular at the time of preparation of the gelling agents, to apply methods which minimise the entry of gaseous inclusions.

The invention, in a further embodiment, therefore relates to a needleless injection device according to the invention, wherein the chamber (11) is completely filled with a gel-like medium (24b).

The invention therefore relates to a method for producing a needleless injection device according to the invention, wherein the (firing) chamber (11) is loaded with a gel-like medium (24b), in particular the (firing) chamber (11) is completely filled with a gel-like medium (24b).

When producing gel-like media according to the invention, such as silicone oleogels, methods are applied which for example minimise the entry of gas into the gel-like media by application of a vacuum. Methods of this type can be carried out both on a small scale (see example 1) and on a large scale in appropriate process facilities.

Within the scope of this invention, the term "pyrotechnic material" is understood to mean any material that can be made to explode with an activation energy. These materials can be, for example, solid or gaseous substances, such as azides, tetrazene, nitrocellulose, picric acid, etc., or other pyrotechnic materials known to a person skilled in the art. It is essential to the invention that the explosion energy allows a sufficiently rapid bulging of the membrane or a sufficient pulse transfer to the membrane (15) according to the invention, such that the substance application (25) can be brought to high speeds and ultimately the substance is detached.

The pyrotechnic material (24a) in accordance with the invention is contained in particular in a chamber (11) that is fully closed outwardly, more specifically in the combustion chamber (24), preferably in the form of a detonator (10). In addition, further or other pyrotechnic material can also be introduced.

It is essential that there is a sufficiently rapid bulging of the membrane up to a sufficiently large pulse transfer to a membrane (15), which can also be formed as a double membrane or multi-layered membrane, such that the particles/substance from the substance application (25) adhering externally in the direction of the target tissue prior to the triggering of the device are sufficiently accelerated, more specifically preferably to speeds of 600 m/s and above.

Within the scope of this invention, the term "pulse (transfer)" is therefore also understood to be synonymous with a transfer or general application of force or pressure which in any case is sufficient to accelerate the substances (25) applied to the skin-side membrane (15) to the desired high speeds and to detach said substances, whereby the substances initially fly freely in the direction of the tissue or skin (18) or body so as to strike there, break through the tissue barrier or body barrier, and infiltrate to the desired depth of the tissue, in particular the skin or the body.

Within the scope of this invention, "skin" means a tissue barrier of a human, mammal or animal outwardly towards the surrounding environment. The skin performs numerous vital functions, and in particular the epidermis, very particularly the stratum corneum (the outer layer of the epidermis), serves as a barrier organ. This barrier function is maintained, inter alia, by skin lipids. These epidermal lipids, such as glycosphingolipids, ceramides, sterols, and sterol esters, fatty acids, triglycerides, n-alkanes, or various polar lipids, are released in the keratinisation process. Due to the needleless or needle-free application according to the invention, these substances consequently can enter the body locally and can then potentially also lead into the bloodstream/and or into the lymphatic systems.

The term "applied substances or substance application (25)" within the scope of this invention means those substances that contain at least one medium and for example are fixed with oils inter alia to the outer (skin-side) membrane (15) or adhere by adhesion. By way of example, the applied substances can contain media which allow a drying of the active substance on said skin-side membrane. In particular, additional adhesion promoters or additives are suitable and can be added, such as oils, carbohydrate solutions, amino acid solutions, polymer solutions, or other preferably pharmaceutically suitable auxiliaries and additives.

The term "substances" includes all agents and media that are suitable for expedient application to the membrane (for example powder, particles, etc.), including one or more active substances (for example medicinal products). The substances are applied to the skin-side membrane (15) and are oriented in front of the membrane, directly opposite the skin. There is no substance application in the direction of the firing chamber (11) or on the firing-chamber-side membrane (13).

The necessary activation energy for pulse transfer can be provided by means of an activation unit, more specifically by means of an igniter or firing pin and via a trigger mechanism by means of friction, impact or suitable power supply.

A suitable activation unit is illustrated in FIG. 1 by way of example. The battery (3) is pressed against a contact spring (6) and against a contact pin (5) by means of a trigger or button (1), thereby closing the electrical circuit via the connections (9) and the EED (10), consequently igniting the EED (10). Alternative triggering mechanisms are known to a person skilled in the art (friction wire, jumper wire, clicker mechanism beating against impact-sensitive ignition mixture, etc).

In a further preferred embodiment, said activation unit (1, 2, 3, 4, 5, 6, 7, 8, 9, 10) is oriented in the axial direction relative to the chamber (11) inclusive of combustion chamber (24), and opposite the membrane (15).

The membrane (15) according to the invention can be fixed or movable or displaceable and can also be formed as a double membrane (13, 15) or multi-layered membrane, and consequently such a membrane in accordance with the invention is the recipient of such a pulse transfer, such that a corresponding acceleration of the substance from a substance application (25 of the skin-side membrane (15) in the direction of the tissue can be created.

In a preferred embodiment, the membrane (15) according to the invention consists of metal or a material of corresponding hardness and ductility, such as steel, plastics, but particularly preferably titanium or sheet titanium. In particular, titanium has an advantageous high formability limit with very good capability of acceleration due to its lower specific density compared with steel with equal mechanical load-bearing capability and better toughness, whereby, with relatively low pressures in the firing chamber, a much quicker speed of the membrane surface or of the buckling membrane is achieved. Here, what is key is the acceleration index AI=yield point sigma0.2/density ro.

Instead of a single membrane, a double membrane can preferably be provided, i.e. for example instead of a single membrane 1 mm thick, two membranes each 0.2 or 0.3 or 0.4 or 0.5 mm thick are placed one over the other so as to form a double membrane. Other thickness ratios are also possible, for example 0.6 mm in the direction of the chamber and 0.4 mm in the direction of the skin or 0.2 and 0.3 mm or 0.3 and 0.4 or 0.4 and 0.5 or 0.2 and 0.6, etc.

A multi-layered membrane is provided in accordance with the invention when more than 2 layers are placed above one another. By way of example, a sealing layers close to the edge or an insulating layer can be introduced between the double membrane in order to modify the speed distribution of the detaching particles.

Here, with the same overall thickness of the membrane, a double membrane combines the advantages of an improved flexibility or deformability with improved safety for the case in which a membrane has a microcrack or obtains one during the deformation. In these cases as well an escape of the high-pressure gas and the pressurised contents from the firing chamber in the direction of the tissue or skin would almost certainly be prevented.

In the case of a fixed double membrane (13, 15), both membranes—the double membrane—are attached/fixed in front of a support disc (16), in particular to the chamber (11), wherein the membrane is slightly movable in the edge region, i.e. can be easily drawn slightly in the direction of the centre during the deformation. It is also preferred that the inwardly directed membrane (13) on the firing chamber side has a thickness of from 0.1 mm to 0.6 mm, preferably 0.2 mm to 0.6 mm, particularly preferably 0.5 mm. The outwardly directed skin-side membrane (15) preferably likewise has a thickness of from 0.1 mm to 0.6 mm, preferably 0.2 mm to 0.6 mm, particularly preferably 0.3 to 0.5 mm. The membranes (13, 15) can contact one another wholly or partially.

In a further preferred embodiment, the inner membrane (13) has a distance from the skin-side membrane (15), more specifically preferably of from 0.2 mm to 1.5 mm, particularly preferably 1 mm. The necessary spacing can be provided by means of a spacer (14) between the two membranes. This measure can mean an efficient prevention of the bursting of the skin-side membrane.

In a further particularly preferred embodiment, the membrane or double membrane (13, 15) is completely or partially curved towards the chamber (11) and into the combustion chamber (24) thereof, over the entire area or preferably in the central radial region about the membrane midpoint. Such a convex curvature of the membranes from the viewpoint of the firing chamber can be achieved by a person skilled in the art by means of known methods and causes a greater acceleration of the membrane surface.

In a further preferred embodiment, the two membranes (13, 15) bear against a support disc (16). This support disc is preferably made of an impact-insensitive plastic having good shock-absorbing properties, such as POM (=Delrin), or metal, for example brass, and has the function of preventing a bursting of the membrane due to the high pressure also applied in the firing chamber or bearing against the membrane after the acceleration of the membrane surface.

At the same time, the support disc (16) can be thinly coated on its inner contour with a soft plastic, for example with polyethylene, so as to advantageously significantly reduce the triggering noise of the device—for example the snap-like noise created when a metal membrane impacts on the surface of a metal support disc is avoided.

The aforementioned embodiments of a membrane or double membrane allow an optimised pulse transfer (see above).

A fundamental and generic construction of a needleless injection device with fixed membrane is shown for example in FIG. 1 together with the key, wherein, for the function of the injection device according to the invention, the housing (22) and also the parts (7) to (16) should be taken into consideration. Here, the parts (7) to (16) can be installed readily in a differently formed housing (22), and a detonator, in particular an EED (10), can also be supplied differently with energy, without modifying the function of the parts or the device. Specific embodiments will be described in greater detail.

The geometry of the individual parts in FIG. 1 can be modified or integrally combined in part depending on the requirements. By way of example, parts (7) to (9) can be integrally combined to form one part, or the part (7) can be omitted, for example if part (8) has an external thread and is screwed into the housing (22) (or for example is held in the housing (22) by retaining ring) or is an insertion part in the injection mould of the housing (22) (see also FIG. 2). The parts (1) and also the parts (4) to (6) and (23) can also be omitted by the use of a conventional button to place the detonator (EED) (10) in electrical contact with the battery (3).

The chamber (11) preferably has O-rings for sealing (12). Furthermore, the chamber (11) can have a vent (20) inclusive of associated cover (21).

In a further preferred embodiment the injection device contains an attachment (17) and/or support disc (16), such that a defined distance, for example of approximately 5-10 mm, is achieved between the skin (18) and the membrane (15) (see above), in order to hold any buckling membrane reliably away from the skin or surface of the body and to obtain a defined flight path of the substances, wherein the membrane is preferably distanced parallel to the skin.

The invention also relates to the use or application of one or more substances, in particular media, active substances, medicinal products for needle-free application by means of the injection device according to the invention in accordance with one of the above embodiments.

The invention also relates to the use or application of substances, in particular materials having any function and suitability, such as dyes or lubricants or materials having other specific properties for needleless insertion into or below the surfaces or body of technical objects by means of the injection device according to the invention in accordance with one of the above embodiments.

The invention therefore relates to an injection device according to any one of the above embodiments for use of a substance, a medium or an active substance, in particular a medicinal product, for needle-free application.

The following examples and drawings are intended to explain the invention in greater detail, but without limiting the invention thereto.

EXAMPLE 1

Figure 1:
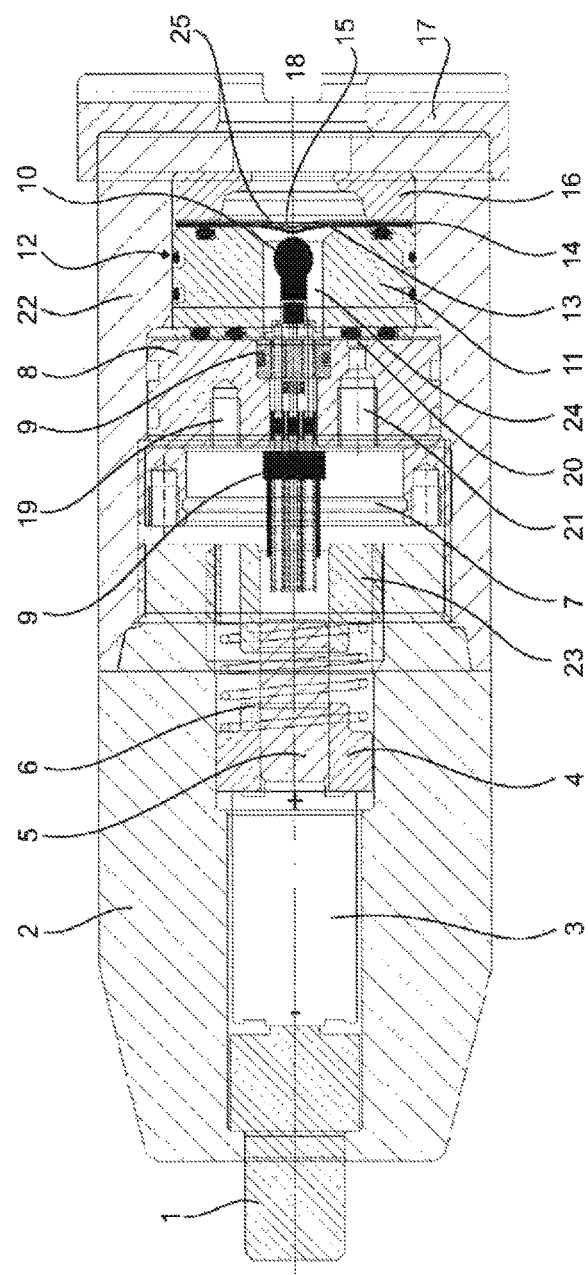
FIG. 1 shows a cross-section of the injection device according to the invention with fixed membrane.
Figure 2:
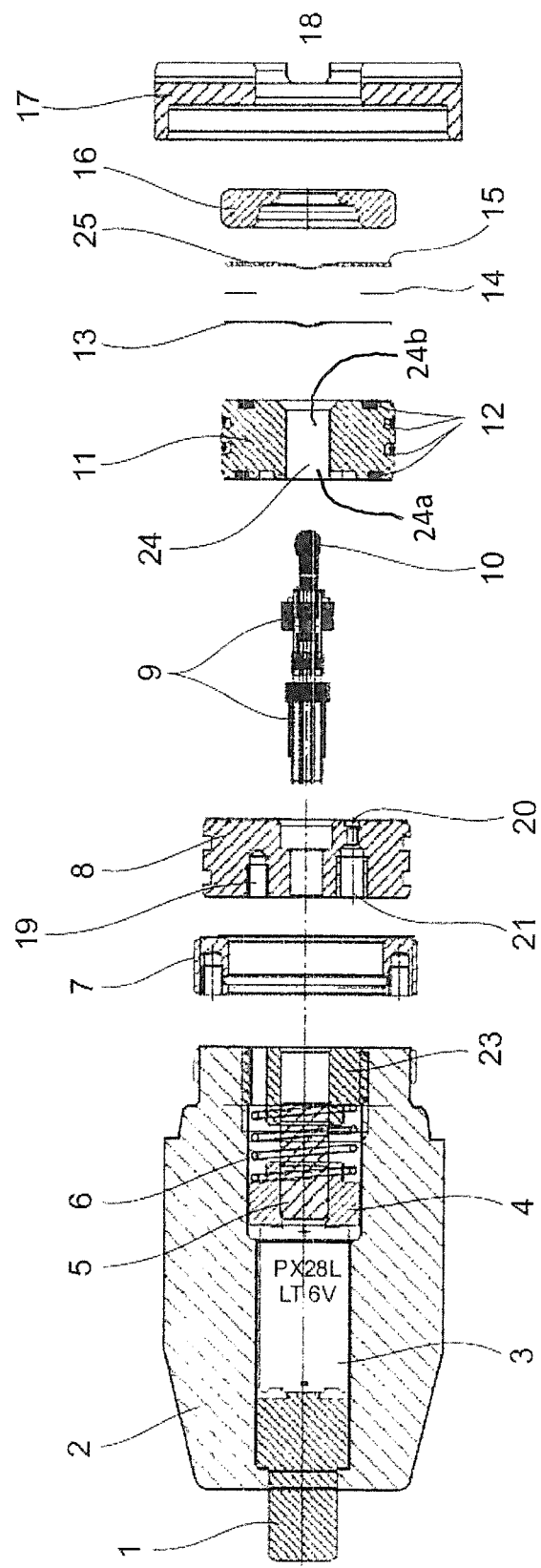
FIG. 2 shows the individual parts of the injection device according to the invention.

Production of bubble-free silicone oleogels having a low air content for the direct filling of the needleless injection device according to the invention.

Silicone Oils

Silicone oil (100 cSt) from Sigma-Aldrich (Sigma-Aldrich, Taufkirchen, Germany)

Silicone oil (500 cSt) from Sigma-Aldrich. (Sigma-Aldrich, Taufkirchen, Germany)

Silicone oil (1000 cSt) from Sigma-Aldrich (Sigma-Aldrich, Taufkirchen, Germany)

Highly Dispersed Silicon Dioxide

Aerosil R200 Pharma (Evonik, Hanau-Wolfgang, Germany)

Aerosil R972 Pharma (Evonik, Hanau-Wolfgang, Germany)

Luer syringe (Norm-Ject) (Henke Sass Wolf, Tuttlingen, Germany)

Luer adapter (Combifix Adapter) (B. Braun, Melsungen, Germany)

Luer stopper (Combi-Stopper) (B. Braun, Melsungen, Germany)

vacuum drying cabinet (Memmert, Schwabach, Germany)

Method:

The plunger of a Luer syringe is removed and the Luer opening is closed by a Luer stopper. The weighed amount of Aerosil is inserted into the Luer syringe from the opening (plunger-side). Depending on the sought concentration, various amounts of Aerosil are weighed in: (4% (m/m), 5% (m/m), 6% (m/m), 10% (m/m). The plunger of the syringe is carefully inserted back into the Luer Lock syringe without severely compromising the Aerosil. The Luer stopper is removed and is replaced by a Luer adapter. A further Luer syringe is connected to the Luer adapter with previously removed plunger. The two connected syringes are secured to a support. The weighed amount of silicone oil (m/m) is poured into the second, empty Luer syringe. The Aerosil is thus combined in the lower Luer syringe with the silicone oil in the upper Luer syringe by means of the Luer adapter.

The connected and filled syringes are placed in a vacuum drying cabinet and are deaerated for at least 4 hours at 10 mbar pressure. Here, the air escapes from the Aerosil and the silicone oil. Due to the adjustment to normal atmosphere, the silicone oil is pushed into the lower Luer syringe chamber containing Aerosil and little air. The silicone oil mixes with the Aerosil and at the same time prevents the infiltration of air into the mixture. The empty upper Luer syringe is removed. A new Luer syringe is connected to the Luer adapter. However, care must be taken to ensure that the Luer adapter is filled up to the edge with the viscous mixture in order to avoid air inclusions by the connection of the new syringe. The silicone oil and Aerosil mixture is pushed 20 times through the Luer adapter into the connected syringe for homogenisation. The Luer syringe and Luer adapter are then removed and the resultant silicone oleogel is closed in the syringe using a Luer stopper. The silicone oleogel can be used directly for the application after the mixing. The gel disposed in the syringe is metered via the Luer cone into the device according to the invention or the firing chamber disposed there by moving the plunger in accordance with the usual function of the syringe.

EXAMPLE 2

Determination of the Viscosity of the Silicone Oleogels

Materials

Silicone oleogels are produced in accordance with the provisions according to Example 1.—4%, 5%, 6% silicone oleogels with Aerosil R200 Pharma 4%, 5%, 6%, 10% silicone oleogels with Aerosil R972 Pharma Equipment Rheometer MCR100 from Anton Pear (Anton Pear, Graz, Austria)

Plate PP50 (Diameter: 49.958 mm)

Working gap 500 μm

Measurement temperature: 250 C

Measurement method: Rising shear rate of 1-100 s−1

A sufficient amount of the oleogel to be examined is applied to the working surface of the rheometer. The plate height is adjusted and any leaking, excess oleogel is carefully removed. A measurement is taken with rising shear rate.—At a shear rate of 36 $s^{-1}$, the following viscosities were determined:

TABLE 1

Viscosities of the silicone oleogels at a shear rate of 36 $s^{-1}$

| Silicone oleoge | Viscosity [Pa s] |
| --- | --- |
| 4% Silicone oleogel (R200 Pharma) | 8.3 ± 0.43 |
| 5% Silicone oleogel (R200 Pharma) | 13.5 ± 0.68 |
| 6% Silicone oleogel (R200 Pharma) | 19.2 ± 1.65 |
| 4% Silicone oleogel (R972 Pharma) | 303.5 ± 8.7 |
| 5% Silicone oleogel (R972 Pharma) | 450.7 ± 37.9 |
| 6% Silicone oleogel (R972 Pharma) | 560.7 ± 38.4 |
| 10% Silicone oleogel (R972 Pharma) | 1645.0 ± 161.3 |

KEY 1 trigger, button
2 trigger housing
3 battery
4 spring cap
5 contact pin
6 contact spring
7 slotted nut
8 holder for glass feedthrough
9 feedthrough of the connections of the EED
10 EED (detonator)
11 firing chamber or chamber
12 O-ring seal of the firing chamber (can also be omitted in some embodiments of the device)
13 inner membrane or firing-chamber-side membrane
14 spacer, also performs sealing functions
15 skin-side membrane, fixed to membrane (13) and spacer (14)
16 support disc
17 attachment
18 skin or surface to be penetrated (bears against 17, not shown)
19 thread for ground connection screw (can also be omitted in some embodiments of the device)
20 firing chamber vent
21 cover, vent
22 housing for the parts 7-21

23 guide for contact pin
24 firing chamber or combustion chamber (24) containing a pyrotechnic substance (24a) and a gel-like medium (24b)
25 substance application in the direction of the tissue or skin

The invention claimed is:

1. A needleless injection device comprising a chamber (11) containing a) at least one pyrotechnic material (24a) and b) at least one gel-like medium (24b), wherein the chamber (11) has at least one membrane (15) at a discharge opening and is provided with a substance application (25), the gel-like medium being selected from the group consisting of gel, oleogel, lipogel, paraffin gel, and silicone oleogel, the gel-like medium comprising a gelling agent and a hydrophobic liquid, the gelling agent being an organic or inorganic gelling agent selected from the group consisting of pectin, tragacanth, polyacrylic acids, polyvinylpyrrolidone, silicon dioxide, highly dispersed silicon dioxide, carboxymethylcellulose, carbomers (polyacrylic acid), cellulose ethers, poloxamers, the gel-like medium being gas-free, the chamber (11) being completely filled with the at least one gel-like medium (24b) and the at least one pyrotechnic material (24a) the at least one membrane being formed as a multi-layered or double membrane comprising an inner membrane (13) and a skin-side membrane (15), the substance application (25) being on a side of the skin-side membrane (15) remote from the inner membrane (13), the inner membrane (13) having a distance from the skin-side membrane (15) of from 0.2 mm to 1.5 mm, the distance being provided by means of a spacer (14) between the two membranes, the spacer (14) functioning to prevent bursting of the skin-side membrane (15), the chamber (11) having a combustion chamber (24), and the spacer (14) being a member having a central open area in line with the combustion chamber (24).

2. The needleless injection device according to claim 1, wherein the hydrophobic liquid is selected from the group consisting of vegetable oils, animal oils, triglycerides, monoglycerides, diglycerides, phospholipids, liquid waxes, alcohols, silicone oils, and paraffins.

3. The needleless injection device according to claim 1, wherein the skin-side membrane (15) consists of steel or plastics.

4. The needleless injection device according to claim 1, wherein the skin-side membrane (15) has a thickness of from 0.1 mm to 0.6 mm.

5. The needleless injection device according to claim 1, wherein inner membrane (13) is located at the combustion chamber (24).

6. The needleless injection device according to claim 1, wherein the at least one of the inner membrane (13) or the skin-side (15) is curved.

7. The needleless injection device according to claim 1, containing an attachment (17) and/or support disc (16), characterised in that during use of the device there can be a distance of at least 5 mm is achieved between the skin (18) of a target patient and the skin-side membrane (15).

8. The needleless injection device according to claim 1, wherein an activation unit (1, 2, 3, 4, 5, 6, 7, 8, 9, 10) is provided in the axial direction relative to the skin-side membrane (15).

9. The needless injection device according to claim 1, wherein the skin-side membrane (15) is made of titanium or sheet titanium.

10. The needless injection device according to claim 1, wherein the inner membrane (13) has a distance from the skin-side membrane (15) of from 0.2 mm to 1.0 mm.

* * * * *